US012765915B2

(12) United States Patent
Zink et al.

(10) Patent No.: US 12,765,915 B2
(45) Date of Patent: Oct. 20, 2026

(54) RECESSION GUIDE APPARATUS AND METHOD OF USE THEREOF

(71) Applicant: DeHeer Orthopedics LLC, Carmel, IN (US)

(72) Inventors: Thomas Zink, Carmel, IN (US); Joseph DeHeer, Carmel, IN (US); Patrick DeHeer, Carmel, IN (US)

(73) Assignee: DeHeer Orthopedics LLC

( * ) Notice: Subject to any disclaimer, the term of this patent is extended or adjusted under 35 U.S.C. 154(b) by 204 days.

(21) Appl. No.: 18/514,129

(22) Filed: Nov. 20, 2023

(65) Prior Publication Data

US 2024/0164807 A1 May 23, 2024

Related U.S. Application Data

(60) Provisional application No. 63/384,239, filed on Nov. 18, 2022.

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01)

(58) Field of Classification Search
CPC ............ A61B 17/3423; A61B 17/3494; A61B 17/3496; A61B 17/02; A61B 17/0218; A61B 17/025; A61B 2017/0256; A61B 2017/0262; A61B 2017/320052; A61B 1/06
See application file for complete search history.

(56) References Cited

U.S. PATENT DOCUMENTS

| | | | | |
|---|---|---|---|---|
| 5,716,329 | A * | 2/1998 | Dieter | A61B 1/303 600/184 |
| 8,876,851 | B1 * | 11/2014 | Woolley | A61B 17/3423 606/198 |
| 9,028,522 | B1 * | 5/2015 | Prado | A61B 17/0206 606/191 |
| 2007/0100366 | A1 * | 5/2007 | Dziedzic | A61B 17/02 606/191 |
| 2013/0274557 | A1 * | 10/2013 | Bowman | A61B 17/0206 600/208 |
| 2015/0374354 | A1 * | 12/2015 | Boyd | A61B 17/1757 600/204 |
| 2016/0270816 | A1 * | 9/2016 | Mather | A61B 90/30 |

(Continued)

*Primary Examiner* — Diane D Yabut
(74) *Attorney, Agent, or Firm* — Gutwein Law; Tyler B. Droste

(57) ABSTRACT

An apparatus comprised of a dilator and a tissue protector component for surgical procedures. The apparatus can be configured for placement in an access to facilitate a spacing of the gastrocnemius and soleus for a recession of one or both of the gastrocnemius and soleus to affect an intramuscular fascial lengthening to improve equinus. The dilator can have an interior cavity with at least one operable window for accessing the cavity. One or more interior apertures can be formed to accept a light source. A tissue protector can be positioned within an insertion channel of the dilator to form a back wall to protect a patient's tissue by placing it between the patient's fascia and associated muscle tissue layers to protect from the surgeon cutting too deep into the patient's muscle tissue.

18 Claims, 14 Drawing Sheets

(56) References Cited

U.S. PATENT DOCUMENTS

| | | | | |
|---|---|---|---|---|
| 2017/0231614 | A1* | 8/2017 | Vogel | A61N 1/0551<br>600/224 |
| 2018/0042631 | A1* | 2/2018 | Garlock | A61B 17/3211 |

* cited by examiner

RECESSION GUIDE APPARATUS AND METHOD OF USE THEREOF

CROSS-REFERENCE

This U.S. patent application claims priority to U.S. Provisional Application 63/384,239 filed Nov. 18, 2022, the disclosure of which is considered part of the disclosure of this application and is hereby incorporated by reference in its entirety.

FIELD OF THE INVENTION

The present disclosure relates generally to an apparatus for use in a surgical procedure for recession. The present disclosure also relates to an apparatus and method for gastrocnemius recession. The apparatus can include a multi-layered retracting and visualization apparatus to achieve reproducible results while reducing invasiveness and risk of overcorrection.

BACKGROUND

Equinus deformity or Talipes equinus, as it is medically and scientifically known, is a condition of the ankle joint in which the range of motion for an upward bending of the ankle (dorsiflexion) is limited. Specifically, equinus is commonly defined as the inability to achieve ankle joint dorsiflexion of less than 90 degrees relative to the distal leg. Equinus can be due to a tightening or tightness within the calf muscles, i.e., the gastrocnemius and/or the soleus.

While there exist non-invasive treatments for the condition of equinus, certain cases do not respond to this style of treatment and surgical intervention is necessary to lengthen the gastrocnemius and/or soleus. Particularly, a gastrocnemius recession, i.e., an incision of the gastrocnemius fascial layer from lateral to medial can be utilized either together, with, or in lieu of a similar soleus recession, i.e., an incision of the soleus fascial layer from lateral to medial. The performance of this procedure requires the separation or spacing of the gastrocnemius and the soleus from one another using some type of retractor. Such conventional, and even existing apparatus modified specifically for this procedure, are not particularly useful for the task and fail to function.

Therefore, what is needed within the art is an improved instrument particularly adapted to adjustably space the gastrocnemius and soleus from one another for recession utilizing, less invasive dissection approach, a spaced guide with depth control, visualization window, and an associated surgical technique.

BRIEF SUMMARY OF THE INVENTION

In one aspect, this disclosure is related to a surgical method utilizing a surgical instrument in the form of an apparatus to facilitate spacing the gastrocnemius and soleus from one another for performing a recession of one or both of the gastrocnemius and soleus to treat equinus. A dilator portion of the apparatus can be inserted between the gastrocnemius and soleus muscles. A tissue protector portion can then be inserted between the fascia layer and the associated muscle of the fascia to protect the surgeon from cutting into muscle tissue, while also creating visualization and space for recession, wherein the tissue protector component forms a protective wall of the patient's muscle tissue.

A user can insert a light source into a portion of the dilator to illuminate the interior cavity of the dilator for surgery.

In another aspect, the present disclosure relates to an apparatus and method for use a recession device to create space and wherein once dilated, a multi-component includes at least dilator having at least one window extending along a portion of a length of the dilator and providing access from an exterior to an interior cavity. Accordingly, a dilator is configured to receive a scalpel for completing a recession of one of the gastrocnemius and/or the soleus to affect a first intramuscular fascial lengthening to relieve equinus. The dilator can feature at least one cavity or cutout which serves for visualization to ensure adequate lengthening was achieved. This and or other layers may feature tunnel like structures that allow for a light source to permeate throughout the apparatus and provide further improved visualization for the surgeon. A removable tissue protector component can be provided to additionally support surrounding tissue and prevent too deep of excision during the procedure. These features may be achieved via additive manufacturing or other means of production.

In another aspect, an apparatus of the present disclosure creates an opening, cut guide with depth control, and a visualization window to perform an intramuscular fascial lengthening to improve ankle joint range of motion caused by equinus deformity.

In yet another aspect, an apparatus of the present disclosure can include a tissue protector component configured to provide protection to a patient's tissue. The tissue protector can have a first end and a second end opposite the first end, a distance between the first end and the second end defining a length of the tissue protector component. The tissue protector component can include a body portion and a tip portion. The tip portion can be generally tapered in configuration. The apparatus can further include a dilator having a body portion and a tip portion. The dilator can include a first end and a second end opposite the first end, a distance between the first end and the second end defining a length of the dilator. The body portion of the dilator can have an interior cavity with a first opening at the second end. A first side wall and a second sidewall can be formed between the first end and second end of the dilator to primarily form the body portion of the dilator. A first operating window can be formed between the first sidewall and second sidewall on a first side of the dilator. On a second side of the dilator, an insertion channel can be formed between the first sidewall and second sidewall. The insertion channel can have a first width configured to accept the tissue protector component.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Figure 1A:
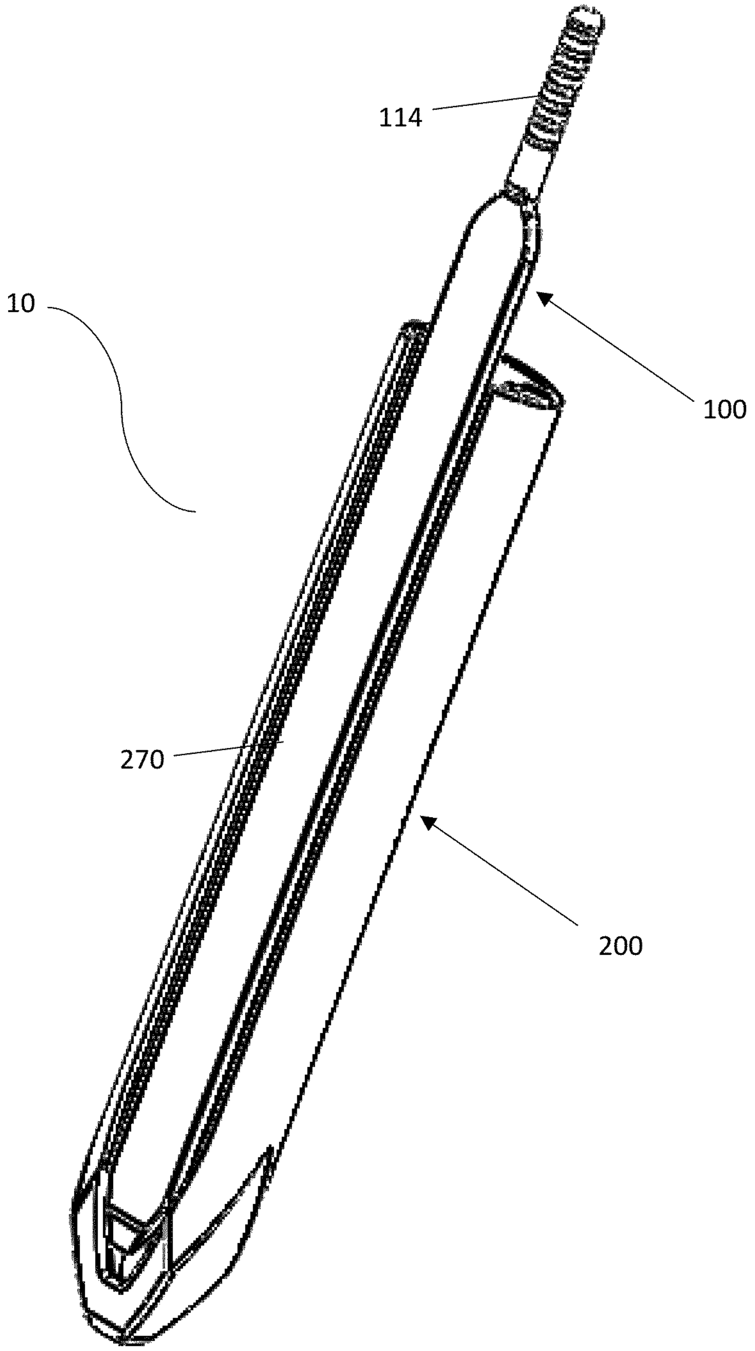
FIG. 1A is a perspective view of an exemplary embodiment of an assembled instrument apparatus according to the present disclosure.
Figure 1B:
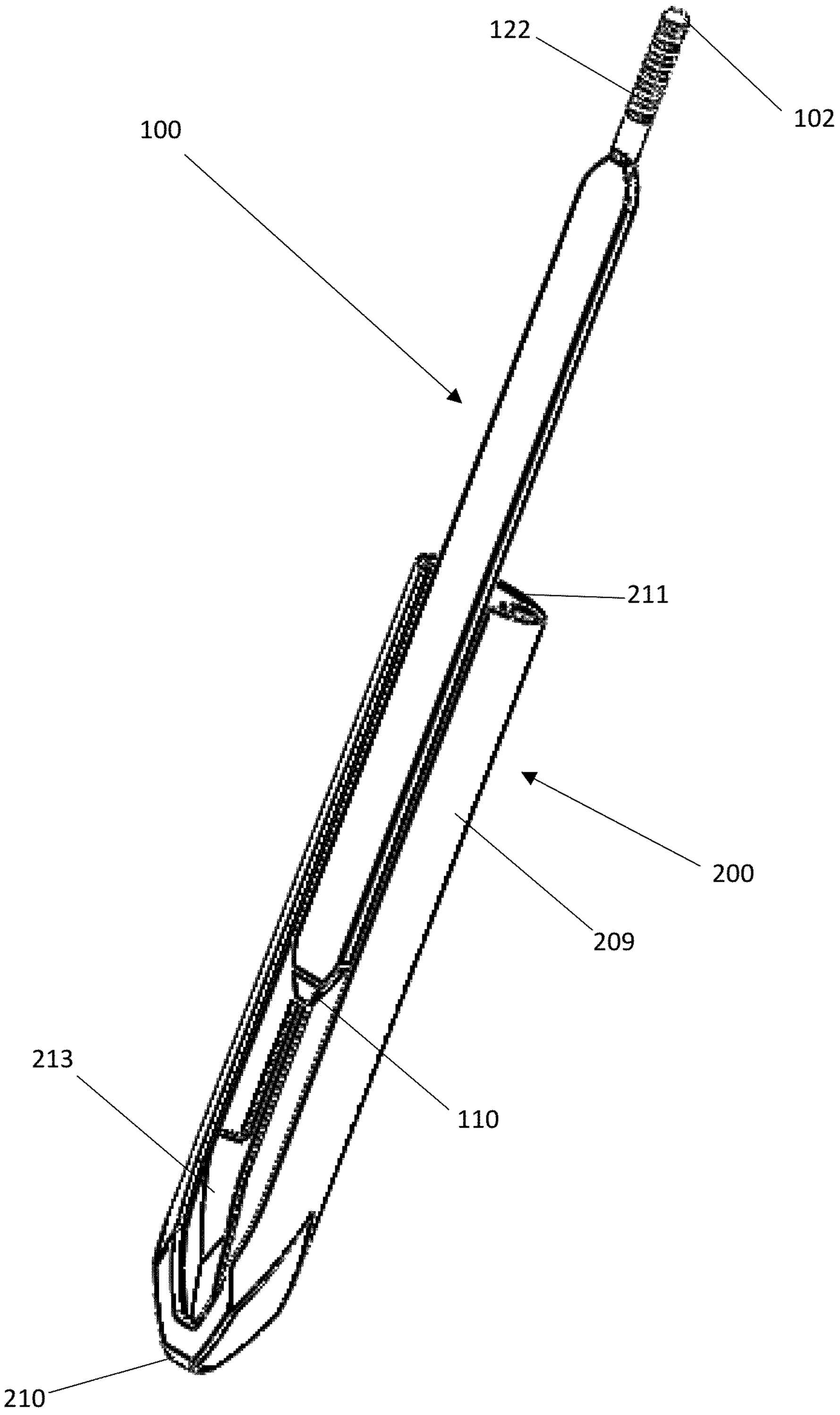
FIG. 1B is a partially exploded view of an exemplary embodiment of an assembled instrument apparatus according to the present disclosure.
Figure 1C:
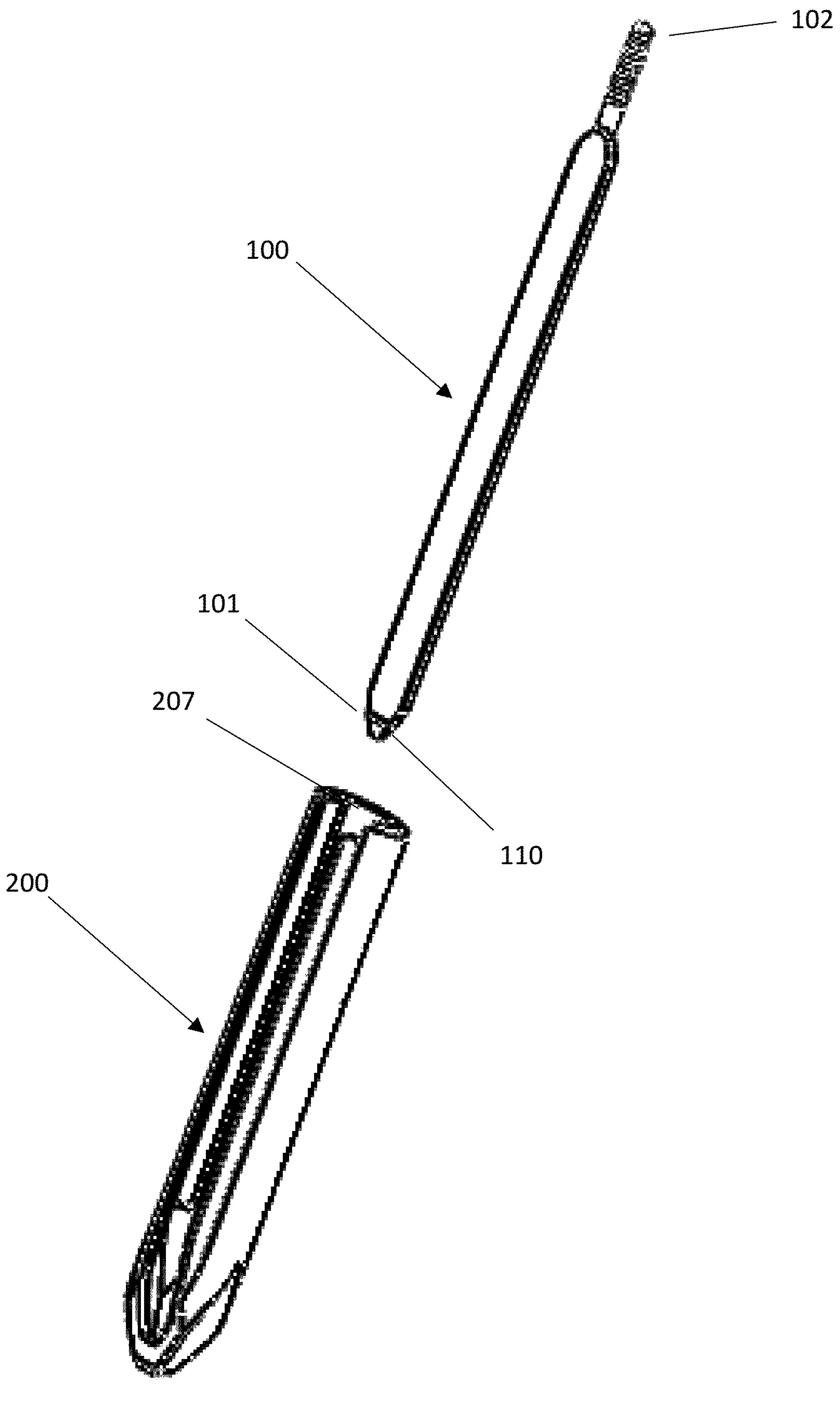
FIG. 1C is a fully exploded view of an exemplary embodiment of an assembled instrument apparatus according to the present disclosure.

The following detailed description includes references to the accompanying drawings, which forms a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention of this disclosure is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful and is not intended to exclude other embodiments from the scope of the invention.

As used herein, the term "coupled" means the joining of two members directly or indirectly to one another. Such joining may be stationary in nature or movable in nature. Such joining may be achieved with the two members, or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Referring now to FIGS. 1-4 of an instrument apparatus and method for use recession procedures including but not limited to treating equinus with the instrument apparatus generally referred to herein as the apparatus 10. An apparatus 10 of the present disclosure can include a two-layer apparatus 10 as shown in FIG. 1A-1C. A two-layer apparatus 10 can comprise a tissue protector component 100 and dilator 200. In some exemplary embodiments, the tissue protector component 100 can be configured to be removably interconnectable with the dilator 200 and form a singular apparatus. In other embodiments, the tissue protector component 100 can be used in conjunction with the dilator 200.

A tissue protector component 100 can generally be probe shaped with a first end 101 and a second end 102 opposite the first end 101, wherein the first end 101 can be tapered to form a tip portion 110. In some exemplary embodiments, the first end can form a tip 110 that can generally be blunt in configuration. Alternatively, the tip 110 can have a slight curvature. The tip portion 110 can have a size and shape that generally allows for guiding and placement within the access in the interval between the fascia and associated muscle of a patient. A distance between the first end 101 and the second end 102 can define a length of the tissue protector component 100, with the length generally allowing for placement within the access and extending exterior to the access to allow for grasping and manipulation by a user to generally place the tissue protector component 100 into a proper surgical position.

Figure 2A:
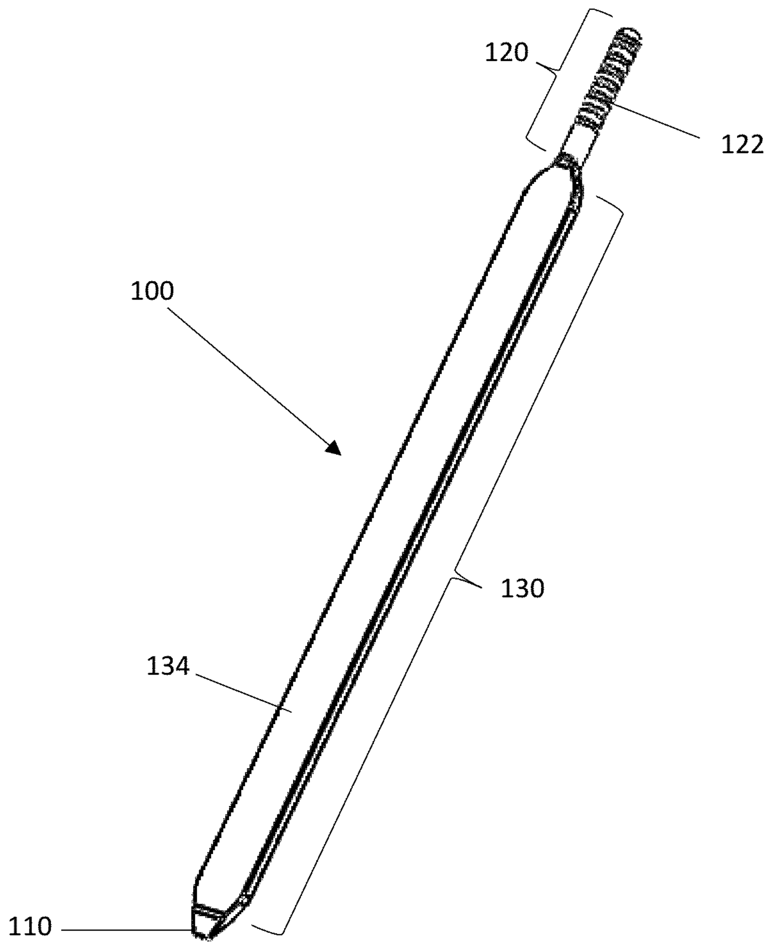
FIG. 2A is a perspective view of an exemplary embodiment of a tissue protector component of the instrument apparatus of the present disclosure.
Figure 2B:
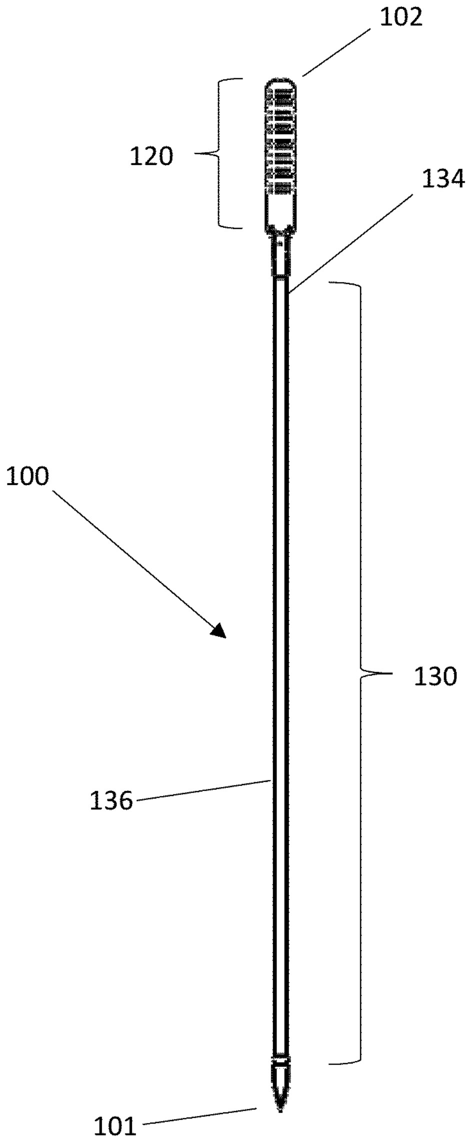
FIG. 2B is a side view of an exemplary embodiment of a tissue protector component of the instrument apparatus of the present disclosure.

In some exemplary embodiments, the second end 102 of the tissue protector component 100 can include a grip portion 120 that can include a textured portion 122 allowing for easier control and grip by a user. The grip portion 120 can take any suitable configuration, including but not limited to a round or rod shape as shown in FIGS. 2A-B. A body portion 130 can be defined between the first end 101 and the second end 102. The body portion 130 can formed below the grip portion 120 and the tip 110 of the tissue protector component 100. The body portion 130 can take any suitable shape including but not limited to a generally planar flat configuration. In some exemplary embodiments, the body portion 130 can have a width greater than the grip portion and a thickness less than the grip portion 120. The body portion 130 can have a first surface 134 and a second surface 136. The edges of the between the first surface can additionally form a third and fourth surface or alternatively a rounded edge between the first surface 134 and second surface 136. The body portion can have a first thickness and a first width. In one exemplary embodiment, the first thickness can be less than the first width. It should be understood that any suitable orientation and dimensions can be utilized.

The body portion 130 can transition generally at an angle tip portion 110. In some exemplary embodiments having four sides, all four sides can angle toward each other to generally form a pyramidal tip portion 110. The tip portion 110 can have a blunt end formed to prevent or limit the ability for the tip to puncture tissue during insertion into a patient.

Figure 3A:
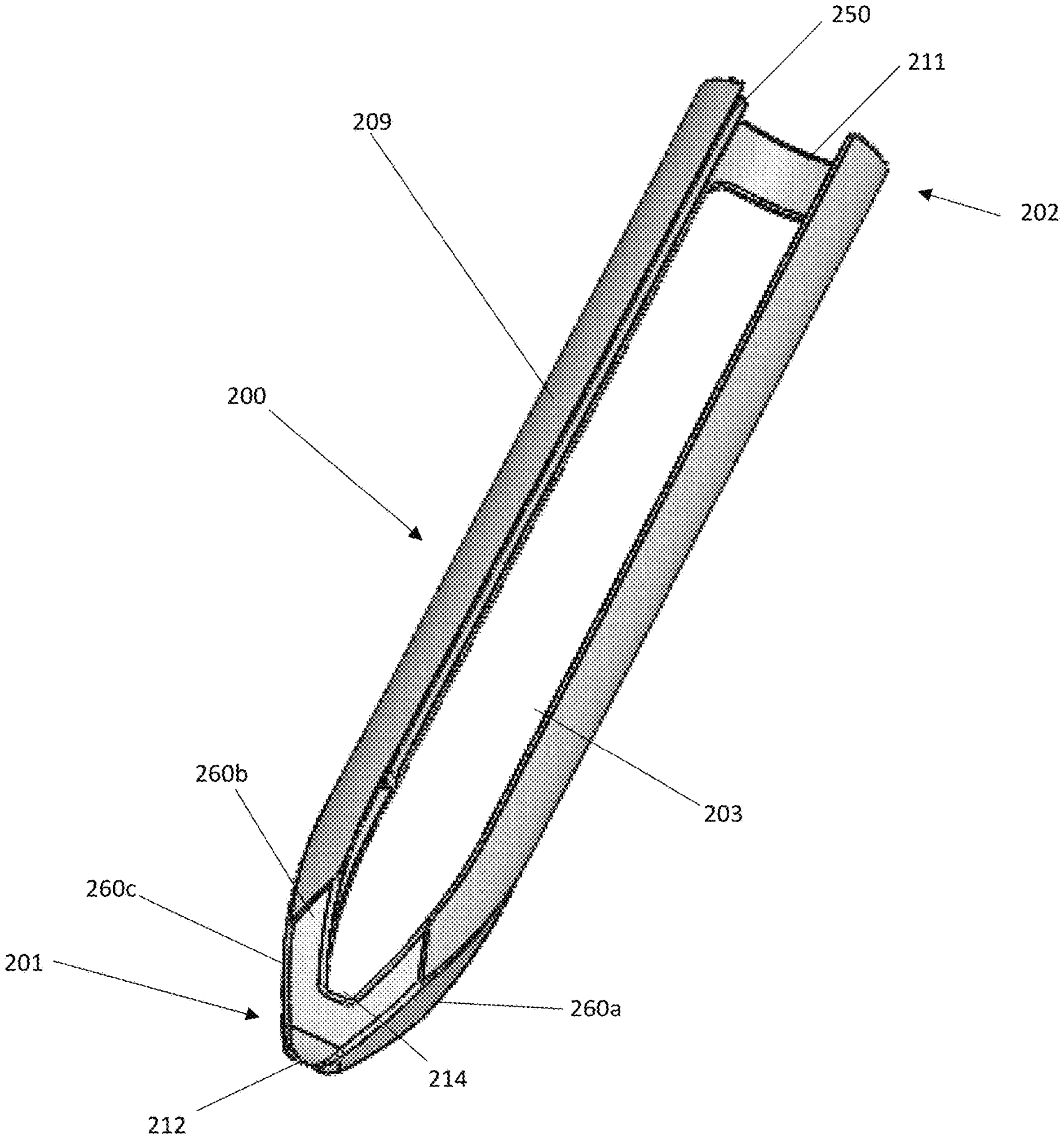
FIG. 3A is a perspective view of an exemplary embodiment of a dilator of the instrument apparatus of the present disclosure.
Figure 3B:
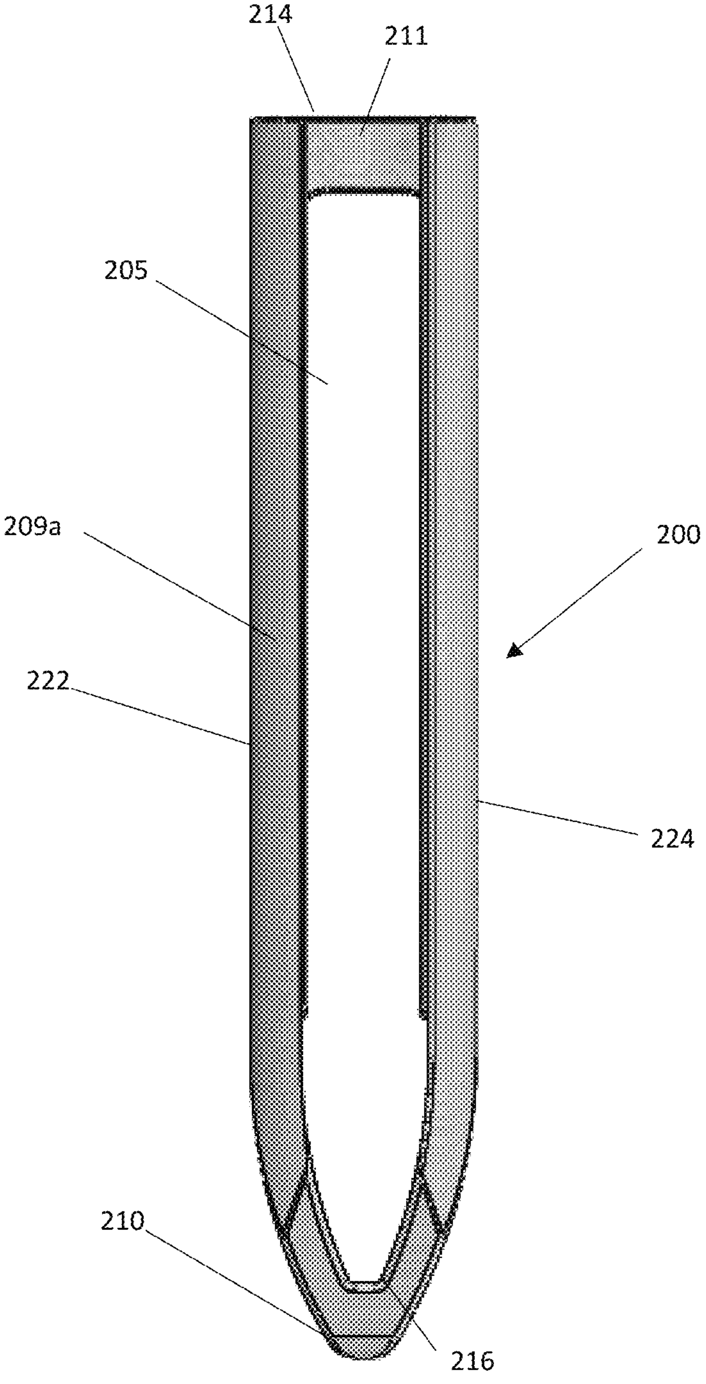
FIG. 3B is a front view of an exemplary embodiment of a dilator of the instrument apparatus of the present disclosure.
Figure 3C:
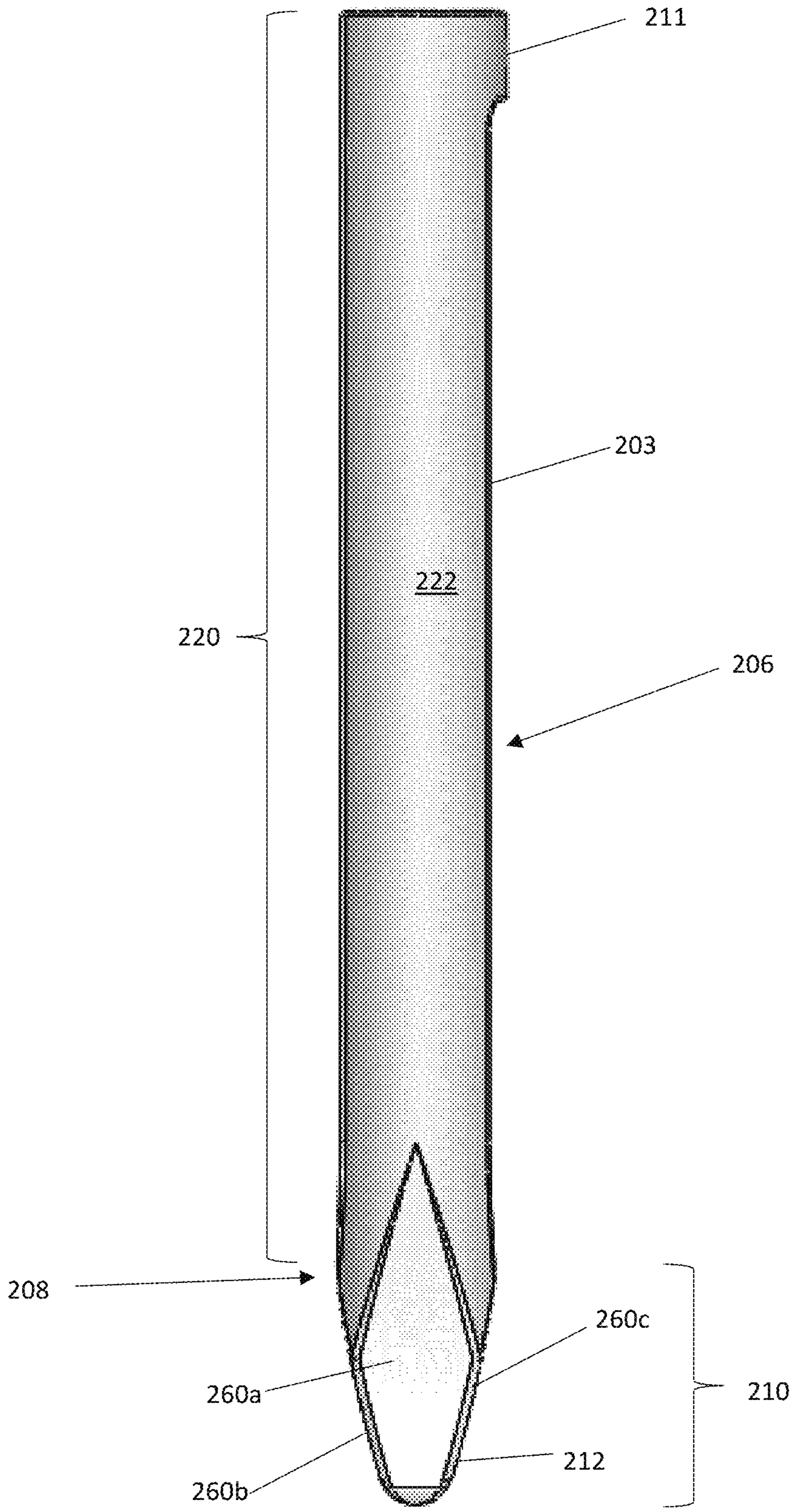
FIG. 3C is a side view of an exemplary embodiment of a dilator of the instrument apparatus of the present disclosure.
Figure 3D:
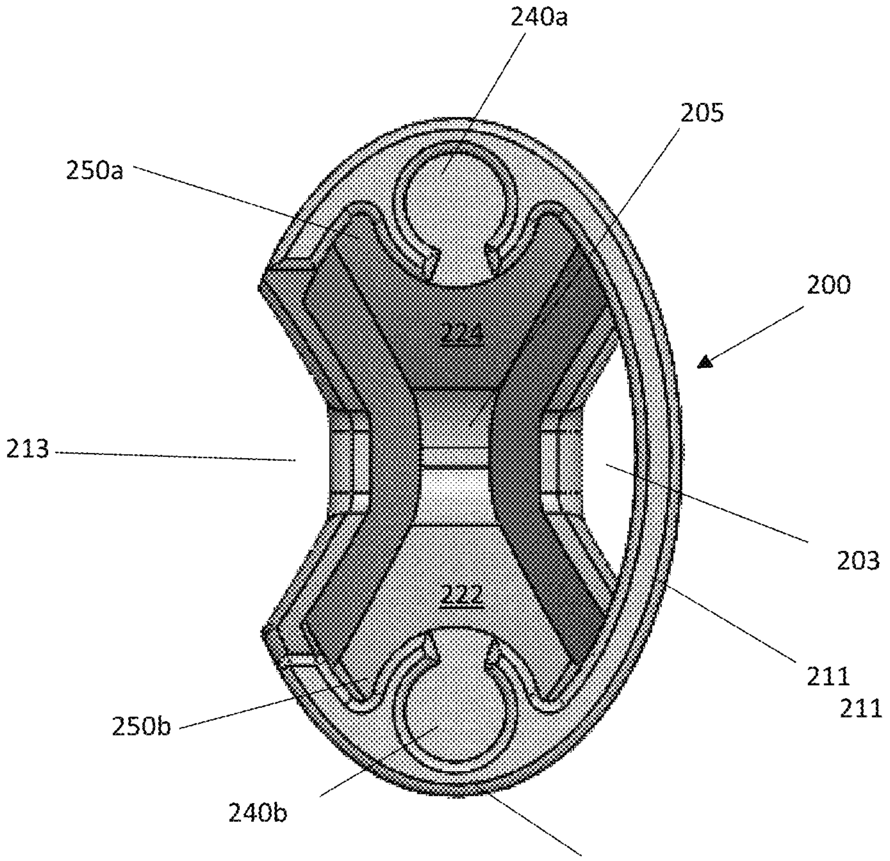
FIG. 3D is a top view of an exemplary embodiment of a dilator of the instrument apparatus of the present disclosure.

As shown in FIGS. 3A-3C, a dilator 200 of a two-layer apparatus 10 of the present disclosure can be sized and shaped to enlarge an interval between the gastrocnemius and the soleus for spacing the gastrocnemius from the soleus in a procedure. The dilator 200 can be used in other procedures to create an operable cavity for the user. In other exemplary uses, a dilator 200 can be inserted on top of a fascia layer to create visualization and space for recession. The dilator 200 can have a first end 201 and a second end 202 opposite the first end 201, a distance between the first end 201 and the second end 202 defining a length of the dilator 200. A dilator 200 can be formed to be hollow a body portion 220 with a first opening 207 at the second end 202 to access the interior cavity 205 and a tip portion 210 at the first end to define an interior cavity 205. A dilator 200 can include at least one window 203 or opening, the at least one window 203 extending along a portion of the length of a dilator 200 of the present disclosure. The window 203 can provide access to perform the prescribed procedure by a user, including but not limited to a recession.

FIG. 3B provides an illustration of a first side 206 of an exemplary embodiment of a dilator 200 of the present disclosure. An exterior surface 209 of the body portion 220 can be formed as a first side wall 222 and a second sidewall 224 with a top edge connection portion 211 to form a window 203 on a first side 206 of the dilator 200. A first side wall 222 can have an interior surface and an exterior surface 209*a* and the second sidewall 224 can have an interior surface and an exterior surface 209*b*. The interior surfaces of the sidewalls 222, 224 can form the cavity 205 within the central portion of the dilator 200. The second side of the dilator 200 can have an insertion channel opening 213 formed between the two sidewalls to allow a path for receipt of a tissue protector component 100 along a length of the dilator 200.

In some exemplary embodiments, the edges of the tissue protector 100 can slide within the grooves 250 and form a back wall 270 to protect the patents tissue one the dilator 200 can be moved into place as shown in FIG. 3A. The channel opening 213 can be formed at the first end 203 of the dilator 200 and extend to form a window 204 on the second side of the dilator 200 and provide a slot opening window 204 to position the tissue protector 100. Alternatively, the tissue protector 100 can be positioned within the channel opening 213 and held in place during a procedure by a user or alternatively maintained in position by the pressure between the muscle once it is put into place after the dilator 200. The dilator 200 can have a generally ovular shape at the first opening 207. The first end 201 can form a tip portion 210 that can similarly approximate the shape of the tip portion 110 of the tissue protector component 100.

The tip portion 110 can include one or more recesses or angular portions 260. The angular portions 260 can extend from each of the sidewalls 222, 224 proximate to the first end 201 to form the tip portion 210. The tip portion 210 can have a generally flat/blunt edge 212 where the angular portions 260 of the sidewall and the angular portions 260 of the top surface and bottom surface meet. The tip portion can generally by pyramidal in configuration forming a blunt or round tip 212 to allow a user to easily position the dilator 200 without potentially puncturing or damaging surrounding anatomy when positioned.

A dilator 200 can optionally have one or more channels or apertures 240 formed along the length of interior cavity 205 to allow for a means of light source 300 for light to travel through the aperture 240 of the dilator 200 and illuminate the workspace within the interior cavity of the dilator 200. In some exemplary embodiments, the interior wall 245 of the apertures 240 can have a reflective coating or reflective adhesive to better reflect or refract the light emitted by the light source 300 to increase the light broadcasted withing the cavity of the dilator 200. In other exemplary embodiments, a prism or reflective material can be formed or positioned within the channels to reflect the light emitted at the top of the channel through the aperture 240.

A dilator 200 can additionally include one or more grooves 250 that can aid in guiding a tissue protector component 100 into position. The grooves 250 can additionally aid in maintain the tissue protector 100 in position once inserted. The grooves 250 can be formed to configure to the edges of the body portion 120 of the tissue protector component 100. In other exemplary embodiments, after a dilator 200 is inserted into the desired position, the tissue protector 100 can be inserted into position within the channel 213 and opening 204 of the dilator 200. The window 204 can a first end located proximate to the first end 214 of the dilator 200 and a second end 216 located at the second end 203 of the dilator 200. The first end 214 of the dilator can approximate the shape of the tip portion 210 and gradually taper to a blunt or flat tip corresponding to the shape of the tip of the tissue protector 100. In other alternative embodiments, the window can be generally planar or rectangular in configuration.

The window 204 can have a width that can be equal to, less than, or greater than the width of the tissue protector 100. In some embodiments, the window width can be greater than the width of the tissue protector 100 body portion 130. In embodiments utilizing the grooves 250 as a holder for the tissue protector 100, the width of the body portion 130 of the tissue protector 100 can be greater than the width of the window 204.

Figure 4A:
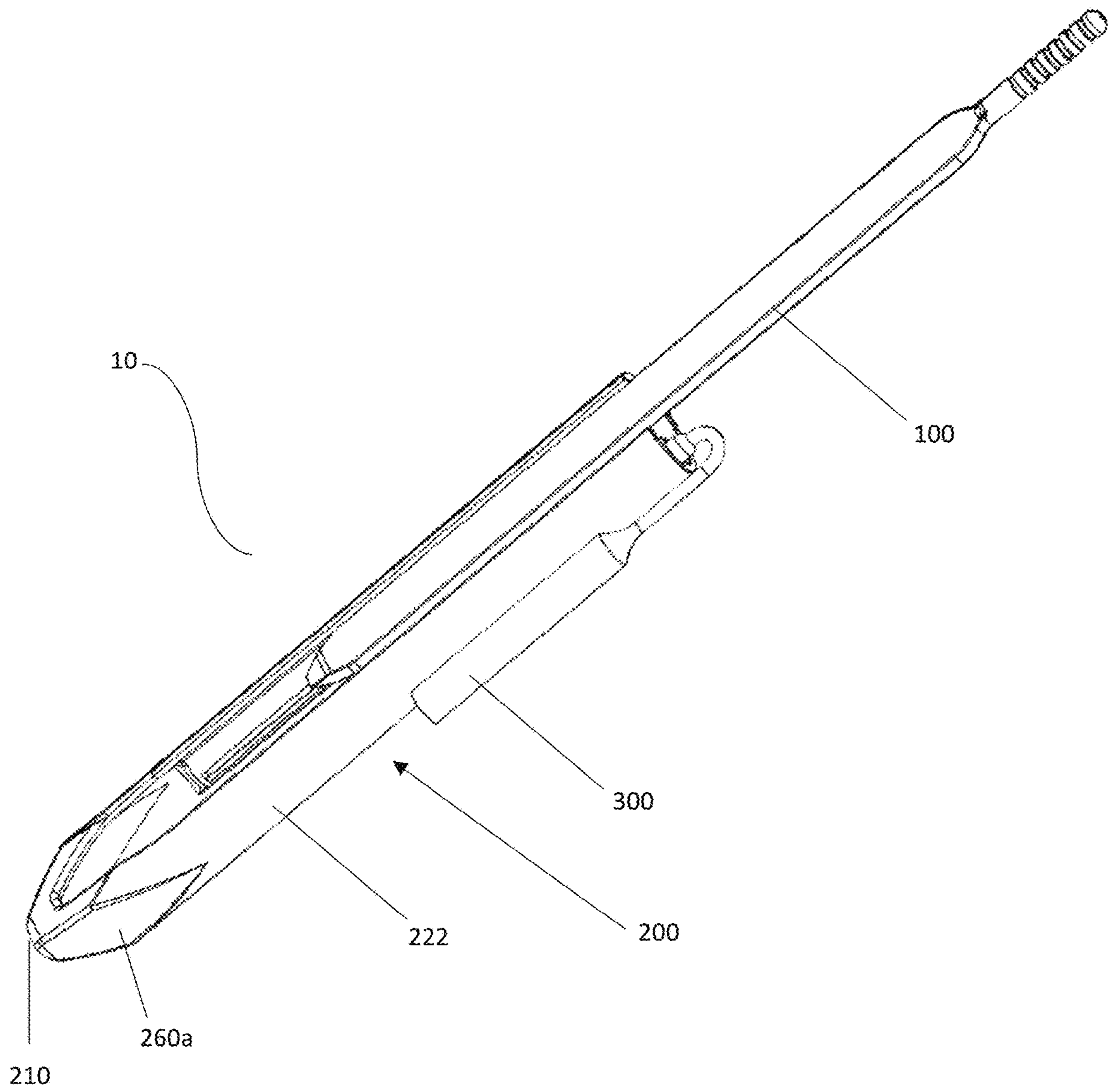
FIG. 4A is a perspective view of an exemplary embodiment of an assembled instrument apparatus according to the present disclosure.
Figure 4B:
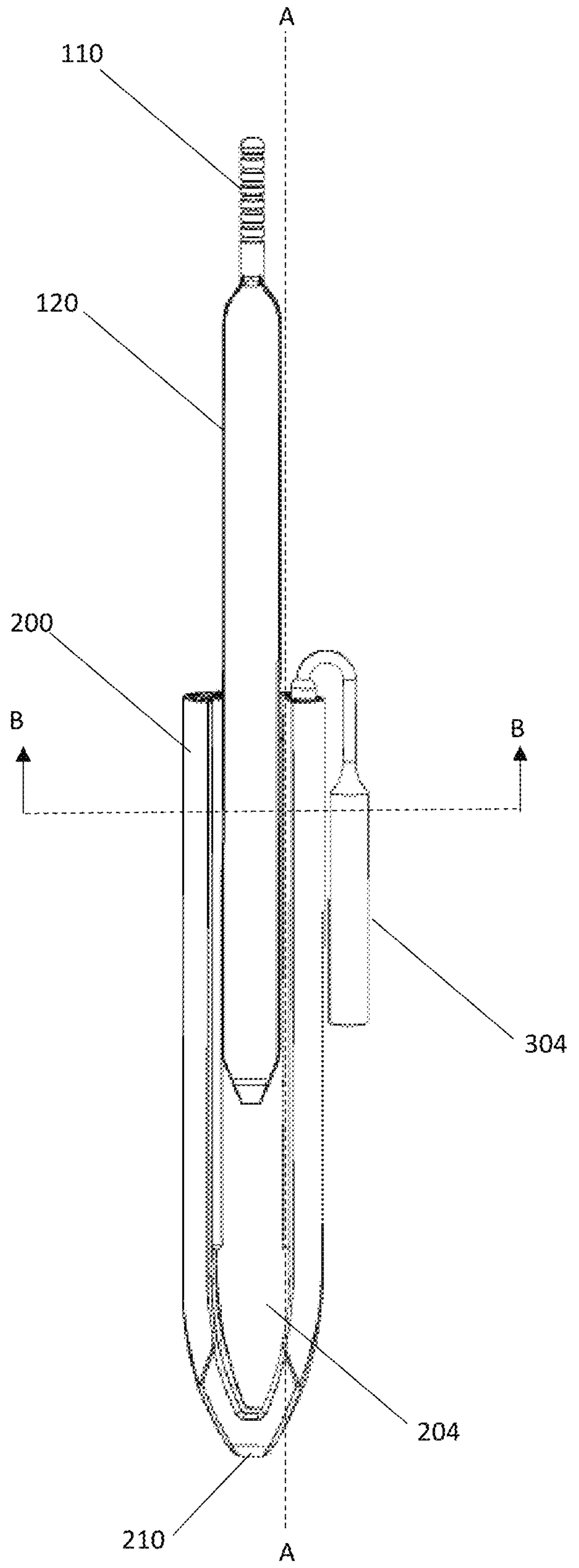
FIG. 4B is a top view of an exemplary embodiment of an assembled instrument apparatus according to the present disclosure.
Figure 4C:
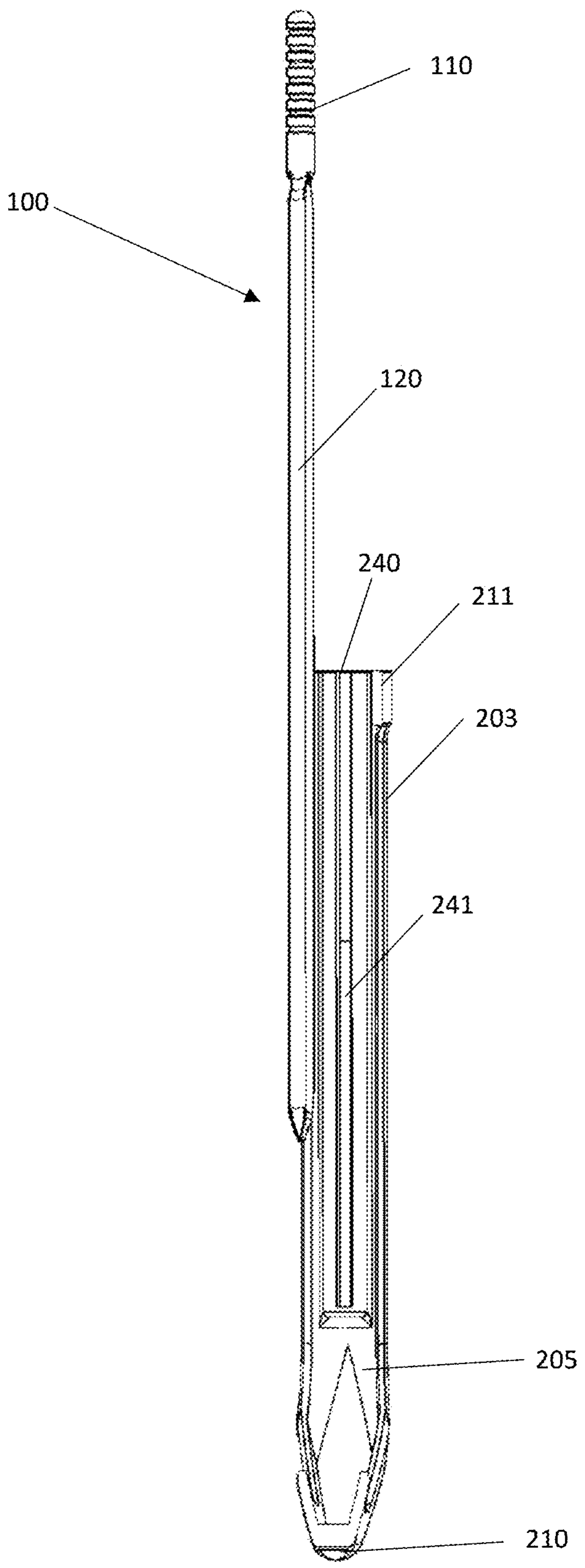
FIG. 4C is a cross-section side view along axis A-A of FIG. 4B of an exemplary embodiment of an assembled instrument apparatus according to the present disclosure.
Figure 4D:
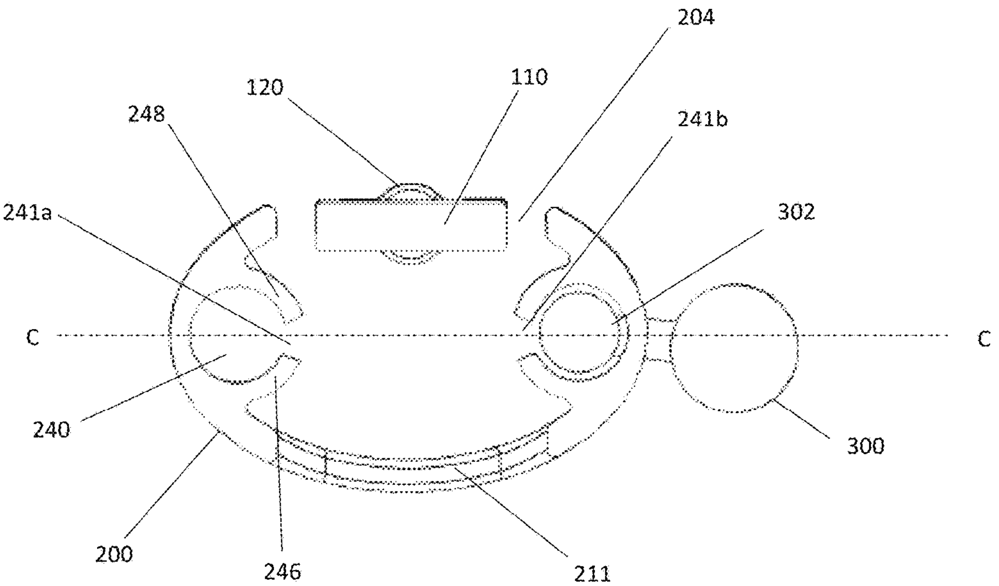
FIG. 4D is a cross-section bottom view along axis B-B of FIG. 4B of an exemplary embodiment of an assembled instrument apparatus according to the present disclosure.
Figure 4E:
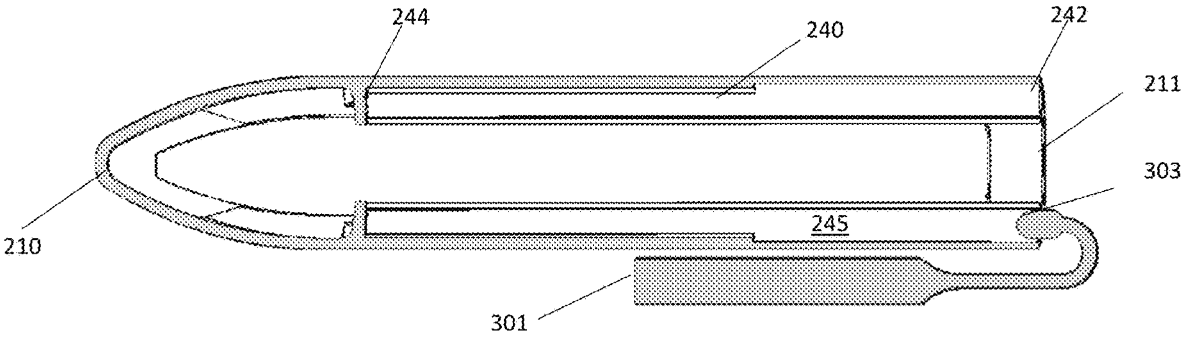
FIG. 4E is a cross-section side view along axis C-C of FIG. 4D of an exemplary embodiment of an assembled instrument apparatus according to the present disclosure.
Figure 4F:
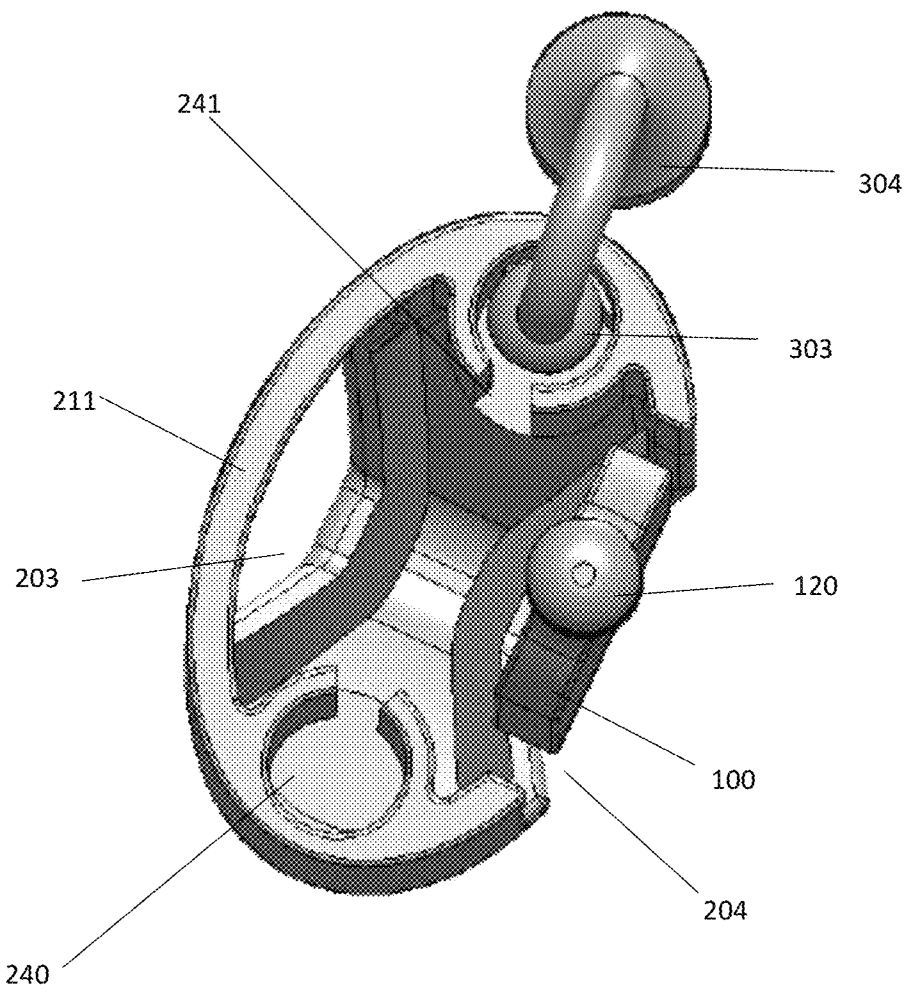
FIG. 4F is a top perspective view of an exemplary embodiment of an assembled instrument apparatus according to the present disclosure.

As shown in FIGS. 4A-4F, an exemplary embodiment of a recession apparatus 10 of the present disclosure can include a tissue protector component or layer 100 and a dilator component or layer 200. In some exemplary embodiments, the apparatus 10 can optionally include a light source 300 that can have a first end 301 and a second end 303. The first end 301 can include a light emitter 302. The light emitter 302 can be any suitable type such as a light emitting diode or other light emitting apparatus. The second end 303 of the light source 300 can be a power supply 304. The power supply 304 can be any suitable power source, including but not limited to a battery or direct power source. As shown in FIGS. 4D-4E, some exemplary embodiments, the first end 301 can be placed within or proximate to one or more of the apertures 240 to provide light to through the aperture 240 and out the channel 241 and into the cavity of the dilator 200. The apertures 240 can have a channel opening 241 from a first end 242 to a second end 244 to allow for the light emitted from a light source 300 illuminate the cavity within the dilator 200. The channel opening 241 can form a first wall 246 and a second wall 248 that approximate a portion of the light source 300. The two walls 246, 248 can extend along the entire or partially between the first end 242 and the second end 244. In other embodiments, the light can be emitted directly into the cavity by the light source 300.

An exemplary method of use for a practitioner of the component apparatus 10 generally utilizes the following steps based upon specific features of the apparatus 10. An access can be created in the proper anatomical location by making an incision to provide access to the muscle layer. An obturator can be optionally used to create an initial channel for the dilator 200. Second, a first end 201 of the dilator 200 can be inserted into the access guided into position on top of the fascia layer to create visualization and space for recession through the operable window and cavity of the dilator 200. Next, a first end 101 of the tissue protector component layer 100 can be inserted into the access and moved into position in the interval between the fascia and an associated muscle and positioned within the insertion channel 213 of the dilator 200. Optional light sources 300 can be inserted into the channels 240 within the dilator 200 for better visualization during the procedure. The surgeon can then cut the fascia within the opening 205 and be prevented or restricted from cutting too deep into muscle due to the protection provided by the tissue protector component 100.

In another exemplary method of use, a practitioner operating with a component apparatus 10 of the present disclosure can generally utilize the following steps based upon specific features of the apparatus 10. First, an access can be created in the proper anatomical location by making an incision to provide access to the muscle layer. The operable window 203 can be aligned into a position relative to the interval between the gastrocnemius and soleus for further spacing the gastrocnemius from the soleus along the sagittal axis. The tissue protector 100 can then be positioned in place within the insertion channel 213 and opening of the dilator 200 to provide a back wall 270 of the apparatus 10 and protect tissue not intended to be part of the procedure and further improve the ease of the procedure of a practitioner. The dilator 200 having at least one window 203 can be utilized to guide a blade for providing a first recession of one of the gastrocnemius and the soleus to affect a first intramuscular fascial lengthening to relieve equinus. A light source 300 can optionally be positioned within one or more apertures 240 to further illuminate the operating cavity 205 during the procedure.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. A recession apparatus, comprising:

a tissue protector component configured to provide protection to a patient's tissue, wherein the tissue protector component includes a body portion, and a tip portion, wherein the tip portion is generally tapered, wherein the tissue protector component includes a first end and a second end opposite the first end, a distance between the first end and the second end defining a length of the tissue protector component; and a dilator having a body portion and a tip portion, wherein the dilator includes a first end and a second end opposite the first end, a distance between the first end and the second end defining a length of the dilator, wherein the body portion of the dilator has an interior cavity with a first opening at the second end, wherein the dilator has a first side and a second side, wherein a first sidewall and a second sidewall can be formed with a first operating window on the first side and a window on the second side, wherein the second side includes an insertion channel having a first width configured to accept the tissue protector component, wherein a top edge connection portion extends between the first sidewall and the second sidewall.

2. The apparatus of claim 1, wherein the first operating window extends along a first side length of the dilator.

3. The apparatus of claim 2, wherein the insertion channel is fully enclosed upon guiding the tissue protector component into the insertion channel of the dilator to form a back wall of the dilator after the dilator has been positioned within the patient's tissue.

4. The apparatus of claim 3, wherein the body portion of the tissue protector component has a first side and a second side and has a flat planar configuration having a first width and first height, wherein the first width is equal to or less than the width of the insertion channel.

5. The apparatus of claim 4, wherein the dilator comprises a first groove and second groove configured to locate and guide the tissue protector component into the insertion channel of the dilator.

6. The apparatus of claim 5, wherein the tip portion of the tissue protector component includes a blunt tip.

7. The apparatus of claim 6, wherein the tip portion of the dilator includes a blunt tip.

8. The apparatus of claim 7, wherein an aperture can form a channel from a first end to a second end within the interior cavity of the dilator, wherein the channel is configured for illumination, and whereby guiding a gastrocnemius recession through the dilator can be illuminated directly through the apparatus.

9. The apparatus of claim 8, wherein the tissue protector component further comprises a grip portion.

10. The apparatus of claim 9, wherein the grip portion of the tissue protector component further includes a textured surface.

11. The apparatus of claim 10, wherein the tissue protector component has generally planar flat body portion at the first end of the tissue protector component.

12. The apparatus of claim 11, wherein the body portion of the tissue protector component has a width greater than the grip portion and a thickness less than the grip portion.

13. The apparatus of claim 12, wherein the grip portion is tubular.

14. The apparatus of claim 8, wherein the dilator is formed of a substantially transparent material, and whereby guiding a gastrocnemius recession through the dilator can be visualized through the substantially transparent material.

15. The apparatus of claim 8, wherein an interior sidewall of the aperture is comprised of a reflective material to reflect light emitted into the aperture out of the channel within the interior cavity of the dilator.

16. The apparatus of claim 15, wherein the reflective material is configured to refract the light into the interior cavity.

17. The apparatus of claim 1, wherein the dilator includes at least one aperture configured to house a light source.

18. An instrument apparatus for facilitating a recession to affect an intramuscular fascial lengthening to relieve equinus, the instrument apparatus comprising:

a dilator having a first end, a second end, a first sidewall, a second sidewall, and an interior cavity, wherein the first sidewall and second sidewall form a tapered tip portion at the first end of the dilator having a first angular portion from the first sidewall, a second angular portion from the second sidewall, a third angular portion from a top surface of the dilator, and a fourth angular portion of a bottom surface of the dilator, wherein the tapered tip portion has a blunt tip, an opening at a second end of an aperture to access the interior cavity of the dilator, a first window is formed on the top surface of the dilator between the tip portion and a top edge connection portion that extends between the first sidewall and the second sidewall and a second window formed on a back surface of the dilator extending from the first end of the dilator to the second end of the dilator providing an insertion channel, wherein the dilator is configured to be positioned in an enlarged interval between a gastrocnemius muscle and a soleus muscle for spacing the gastrocnemius muscle from the soleus muscle;

a tissue protector component, the tissue protector component probe shaped and having a first end generally tapered from a second end to the first end culminating in a blunt tip at the first end with the tissue protector component sized and shaped to be positioned within the insertion channel of the dilator and in an interval between a fascia and an associated muscle to the fascia; and a light emitting apparatus, wherein the interior cavity of the dilator includes one or more channels extending along an interior side wall of the interior cavity between the first end and second end configured to interface with the light emitting apparatus to illuminate the interior cavity of the dilator.

* * * * *